US009089253B2

(12) United States Patent
Hashimoto

(10) Patent No.: US 9,089,253 B2
(45) Date of Patent: Jul. 28, 2015

(54) ULTRASONIC DIAGNOSTIC APPARATUS AND METHOD OF CONTROLLING THE SAME

(75) Inventor: Shinichi Hashimoto, Otawara (JP)

(73) Assignees: KABUSHIKI KAISHA TOSHIBA, Tokyo (JP); TOSHIBA MEDICAL SYSTEMS CORPORATION, Otawara (JP)

( * ) Notice: Subject to any disclaimer, the term of this patent is extended or adjusted under 35 U.S.C. 154(b) by 1012 days.

(21) Appl. No.: 12/358,738

(22) Filed: Jan. 23, 2009

(65) Prior Publication Data

US 2009/0192386 A1 Jul. 30, 2009

(30) Foreign Application Priority Data

Jan. 25, 2008 (JP) .................... 2008-015151

(51) Int. Cl.
*A61B 8/00* (2006.01)
*A61B 8/08* (2006.01)

(52) U.S. Cl.
CPC . *A61B 8/00* (2013.01); *A61B 8/483* (2013.01); *A61B 8/5276* (2013.01); *A61B 8/543* (2013.01); *A61B 8/0883* (2013.01)

(58) Field of Classification Search
USPC ........................................ 600/407, 437–461
See application file for complete search history.

(56) References Cited

U.S. PATENT DOCUMENTS

| 6,228,028 B1 * | 5/2001 | Klein et al. .................... 600/437 |
| 6,544,175 B1 | 4/2003 | Newman |
| 2005/0049502 A1 * | 3/2005 | Schoisswohl ................. 600/453 |

FOREIGN PATENT DOCUMENTS

| JP | 3046424 | 3/2000 |
| JP | 2007-20908 | 2/2007 |

* cited by examiner

*Primary Examiner* — Mark Remaly
(74) *Attorney, Agent, or Firm* — Oblon, McClelland, Maier & Neustadt, L.L.P.

(57) ABSTRACT

In an ultrasonic diagnostic apparatus including an ultrasonic probe, a scan controller, a storage unit, and an image generation unit, the scan controller receives a trigger signal every heartbeat period, scans each of a predetermined number of blocks of a particular diagnostic region of a body under examination with an ultrasonic beam a plurality of times in response to the trigger signal. The storage unit converts an acquired reflection signal into image data and stores the image data of an amount corresponding to a period in which the body under examination is fully scanned a plurality of times. The image generation unit selects image data from the image data stored in the storage unit for the respective blocks in accordance with the spatial arrangement order without being restricted by the temporal acquisition order, and generates a full image of the body under examination by connecting the selected image data.

6 Claims, 10 Drawing Sheets

FIG. 6

ULTRASONIC DIAGNOSTIC APPARATUS AND METHOD OF CONTROLLING THE SAME

BACKGROUND OF THE INVENTION

1. Field of the Invention

The present invention relates to an ultrasonic diagnostic apparatus and a control method thereof, and more particularly, to an ultrasonic diagnostic apparatus configured to three-dimensionally scan the inside of a body under examination using an ultrasonic wave in response to a trigger signal generated based on an electrocardrgram signal or the like, and a method of controlling such an ultrasonic diagnostic apparatus.

2. Description of the Related Art

In recent years, an ultrasonic diagnostic apparatus capable of displaying a three-dimensional moving image has been in active development, and it has become possible to display a three-dimensional diagnostic image with higher resolution over a larger region than in conventional two-dimensional images.

The ultrasonic diagnostic apparatus generates a diagnosis image using an ultrasonic wave propagating in a living body, and thus the time from the transmission of an ultrasonic pulse to the reception of a reflected wave from a living body is basically the same for a three-dimensional ultrasonic diagnostic apparatus and a two-dimensional ultrasonic diagnostic apparatus. To scan a three-dimensional region in a living body with high resolution, a great number of scanning beams are required. Thus, the three-dimensional ultrasonic diagnostic apparatus generally needs a longer time to scan a specified region than the two-dimensional ultrasonic diagnostic apparatus needs. In other words, when the spatial resolution is equal, the frame rate of the three-dimensional image (i.e., the frequency at which the three-dimensional image is updated) obtained by the three-dimensional ultrasonic diagnostic apparatus is theoretically lower than the frame rate of the two-dimensional image obtained by the two-dimensional ultrasonic diagnostic apparatus.

To solve the problem described above, various techniques have been proposed (see, for example, U.S. Pat. No. 6,544,175, JP-A 2007-20908, JP 3,046,424 B etc.). A basic idea of these techniques is to divide a full region (volume) under examination for diagnosis (hereinafter, referred to simply as a full volume) into a plurality of small regions (hereinafter referred to as sub volumes), and obtain a three-dimensional image of the full volume by connecting image data obtained by scanning three-dimensional space of the sub volumes at a high frame rate. In this technique, the observation time of sub volumes is different from each other. Therefore, it is important to connect sub volumes so that good spatial continuity is achieved.

Depending on a part under diagnosis, the part can move due to breathing or a heartbeat. To avoid a problem due to the motion of the part under diagnosis, for example, U.S. Pat. No. 6,544,175 discloses a technique to acquire a plurality of image data in a sub volume in synchronization with the motion of a heart. In this technique disclosed in U.S. Pat. No. 6,544,175, a three-dimensional moving image of a heart is produced in real time as described briefly below.

In this technique, a signal of an electrocardiogram, i.e., an ECG signal is used as a signal synchronous with motion of a heart. More specifically, an R-wave signal, which appears at the end of a diastolic period, is used as an ECG trigger signal.

A three-dimensional full volume of a heart under examination is divided into four sub volumes, and image data of one heartbeat is captured in synchronization with the ECG trigger signal for each sub volume. Note that the image data of one heartbeat includes a plurality of frames of images. For example, 20 frames of images of one sub volume are obtained by repeatedly scanning the sub volume 20 times for one heartbeat (during one interval of the ECG trigger signal). In this case, if the repetition period of the heartbeat is assumed to be one second, the image data of each sub volume is obtained at a frame rate of 20 fps, which is reasonably high to obtain a moving image representing motion of a heart.

The plurality of frames of image data obtained for each sub volume are connected to obtain a full volume of image data as follows. That is, frame images that are same in "time phase" are extracted from the plurality of fame images of sub volumes and are connected together so as to obtain a frame image of the full volume. The "time phase" refers to a delay with respect to a time at which an ECG trigger signal is generated. The motion associated with contraction and relaxation of the heart normally has periodicity synchronous with the ECG trigger signal. Therefore, by extracting frame images which are equal in the time phase from the respective sub volumes and connecting the extracted frame images, it is possible to obtain good spatial continuity between the sub volumes. In practice, successive "time phase numbers" are assigned to frame images in scanning order from one closest to an ECG trigger signal, and an image of a full volume is synthesized by connecting frame images having an equal time phase number. For example, in a case where the full volume is divided into four sub volumes A, B, C, and D and each sub volume is scanned repeatedly 20 times, a total of twenty frame images with time phase numbers of 0 to 19 are obtained for each sub volume. Frame images with each equal time phase number are extracted from the sub volumes A, B, C, and D and the extracted frame images are connected together thereby obtaining a synthesized image of the full volume corresponding to the time phase number. The combining of frame images is performed for each of the time phase numbers so as to obtain synthesized full volume images with time phase numbers from 0 to 19. Thus, a total of twenty synthesized full volume frame images are obtained for each ECG trigger signal. Note that the frame rate of the full volume images is equal to that of the sub volume images. Thus, for example, a full volume moving image with a frame rate of 20 fps is obtained.

As described above, in the conventional techniques, each sub volume is scanned a plurality of times in response to each ECG trigger signal so that each scanning provides one frame image (a frame image of a sub volume). The number of repetitions of scanning for each sub volume is predetermined based on the period of the ECG trigger signal before diagnosis using a three-dimensional image is started.

However, our heartbeat period is not necessarily constant. On the contrary, even persons with a normal and healthy body have a variation of about 10% in the heartbeat period. In the case of patients having a disease such as arrhythmias, a greater variation in heartbeat period can occur. Thus, the period of the ECG trigger signal also varies according to the variation in heartbeat period.

Therefore, the number of repetitions of scanning for each sub volume is not necessarily equal to a value determined before diagnosis is started. For example, even if the number, N, of repetitions of scanning for each sub volume is set to 20 before diagnosis is started, the number, N, of repetition of scanning can vary to a lower value such as 18 or a higher value such as 22 depending on a variation in heartbeat period occurring after the diagnosis is started. This can cause such a problem that when frame images with the same phase number are tried to be connected, there is no scanning data for some sub volume.

For example, if the heartbeat period is short in a scan period for a sub volume A and thus scanning data is obtained for only time phase numbers from 1 to 18, and if the heartbeat period becomes longer for sub volumes B, C, and D following the sub volume A and thus scanning data is obtained for all time phase numbers from 1 to 20, then the following problem can occur. When it is attempted to produce a full volume image by connecting frame images with a time phase number 19 or 20, it is impossible to achieve spatial continuity in the full volume because there is no frame image with a time phase number 19 or 20 for the sub volume A. Furthermore, for example, in the sub volume A, the maximum obtainable time phase number varies depending on the fluctuation of the heartbeat period, and thus scanning data can be acquired only up to the time phase number 18 in a particular period, while scanning data can be acquired up to the time phase number 20 in another period. As a result, when the full volume image is displayed in the form of a moving image, temporal continuity is not obtained in the sub volume A.

As described above, in the conventional techniques, there is a possibility that spatial or temporal discontinuity occurs in the image due to fluctuations of the heartbeat period. The discontinuity of the image can cause a problem in diagnosis using the image.

In view of the above, it is an object of the present invention to provide an ultrasonic diagnostic apparatus capable of preventing or reducing spatial/temporal discontinuity in a synthesized image regardless of a fluctuation of the heartbeat period, and a method of controlling such an ultrasonic diagnostic apparatus.

SUMMARY OF THE INVENTION

In an aspect of the present invention, there is provided an ultrasonic diagnostic apparatus including an ultrasonic probe configured to scan an ultrasonic beam in a main scanning direction and a sub scanning direction and detect a reflection signal from the inside of a body under examination, a scan controller configured to input a trigger signal output every heartbeat period from the outside, scan the ultrasonic beam such that each of a predetermined number of blocks obtained by dividing a particular diagnostic region of the body under examination is scanned repetitively with the ultrasonic beam a plurality of times for a period from one trigger signal to a next trigger signal, a storage unit configured to convert the reflection signal, acquired in accordance a the repetitive scanning order and a block arrangement order, into image data and store the image data of an amount corresponding to a period in which the body under examination is fully scanned a plurality of times, and an image generation unit configured to select blocks in accordance with the spatial arrangement order without being restricted by the temporal acquisition order, extract image data that is equal in the repetition scanning order from the image data of the respective selected blocks stored in the storage unit, and generate a full image of the body under examination by connecting the extracted image data thereby updating the full image.

In an aspect of the present invention, there is provided a method of controlling an ultrasonic diagnostic apparatus, including the steps of (a) scanning an ultrasonic beam in a main scanning direction and a sub scanning direction and detecting a reflection signal from the inside of a body under examination, (b) inputting a trigger signal output every heartbeat period from the outside, (c) scanning the ultrasonic beam such that each of a predetermined number of blocks obtained by dividing a particular diagnostic region of the body under examination is scanned with the ultrasonic beam a plurality of times for a period from one trigger signal to a next trigger signal, (d) converting the reflection signal, acquired in accordance with the repetitive scanning order and the block arrangement order, into image data and storing the image data of an amount corresponding to a period in which the body under examination is fully scanned a plurality of times, and (e) selecting blocks in accordance with the spatial arrangement order without being restricted by the temporal acquisition order, extracting image data that is equal in the repetition scanning order from the image data of the respective selected blocks stored, and generating a full image of the body under examination by connecting the extracted image data thereby updating the full image.

In the ultrasonic diagnostic apparatus and the method of controlling it according to the present invention, it is possible prevent or reduce spatial/temporal discontinuity in a synthesized image regardless of a fluctuation of the heartbeat period.

BRIEF DESCRIPTION OF THE DRAWINGS

FIG. 6 is a diagram illustrating a second example of a modification to the method (first method) of synthesizing a full volume image;

DESCRIPTION OF THE EMBODIMENTS

Embodiments of an ultrasonic diagnostic apparatus and a control method thereof according to the present invention are described below with reference to the accompanying drawings.

General Configuration

Figure 1:
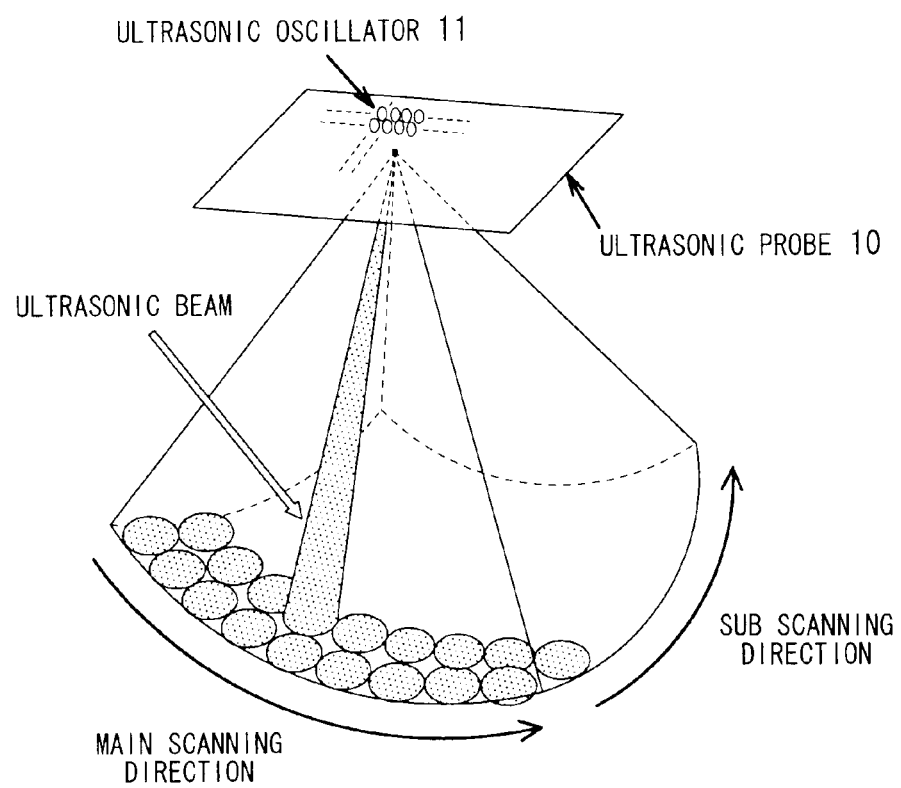
FIG. 1 is a diagram schematically illustrating a beam scanning operation of a three-dimensional ultrasonic diagnostic apparatus.

FIG. 1 is a diagram schematically illustrating an ultrasonic beam scanning operation of an ultrasonic diagnostic apparatus 1 according to an embodiment of the present invention. The ultrasonic diagnostic apparatus 1 generates a fine ultrasonic beam using an ultrasonic probe 10 including a two-dimensional array of ultrasonic oscillators 11. The generated ultrasonic beam is directed to a target part of a body under examination while being electronically deflected so that the part under examination is scanned by the ultrasonic beam in a main scanning direction and a sub scanning direction. From a reflection signal from the part under examination, three-dimensional information in terms of the main scanning direction, the sub scanning direction, and the distance is obtained.

In a conventional one-dimensional ultrasonic probe, ultrasonic oscillators are arranged in the form of a one-dimensional array and scanning is performed within a plane. In contrast, in the two-dimensional ultrasonic probe 10 according to the present embodiment of the invention, scanning is performed in a three-dimensional volume. Furthermore, because the ultrasonic beam used in the scanning has a small beam width, it is possible to obtain three-dimensional information with high resolution over a large region. From the obtained three-dimensional information, it is possible to produce a three-dimensional image viewed from an arbitrary direction or an image of an arbitrary cross section thereof.

However, because the ultrasonic beam is scanned in both directions, i.e., in the main scanning direction and the sub scanning direction, the number of beam positions in the whole region under examination (the full volume) is much greater than that in the case in which the beam is scanned in a plane. Therefore, if the scanning is simply performed sequentially from a start point to an end point in the full volume, it takes a long time to completely scan the full volume, and thus the frame rate of the image of the full volume becomes low.

In the ultrasonic diagnostic apparatus 1 according to the present embodiment of the invention, to solve the above problem, as described above, the full volume is divided into a plurality of sub volumes (four sub volumes, for example) and each sub volume is scanned at a high frame rate (20 fps, for example). Frame images obtained for the respective sub volumes are connected so as to obtain a synthesized frame image of the full volume. The resultant image of the full volume has a high frame rate (20 fps, for example) equal to that of the sub volumes, and thus it is possible to produce a three-dimensional moving image in real time for even a moving region such as a heart under examination for diagnosis.

Figure 2:
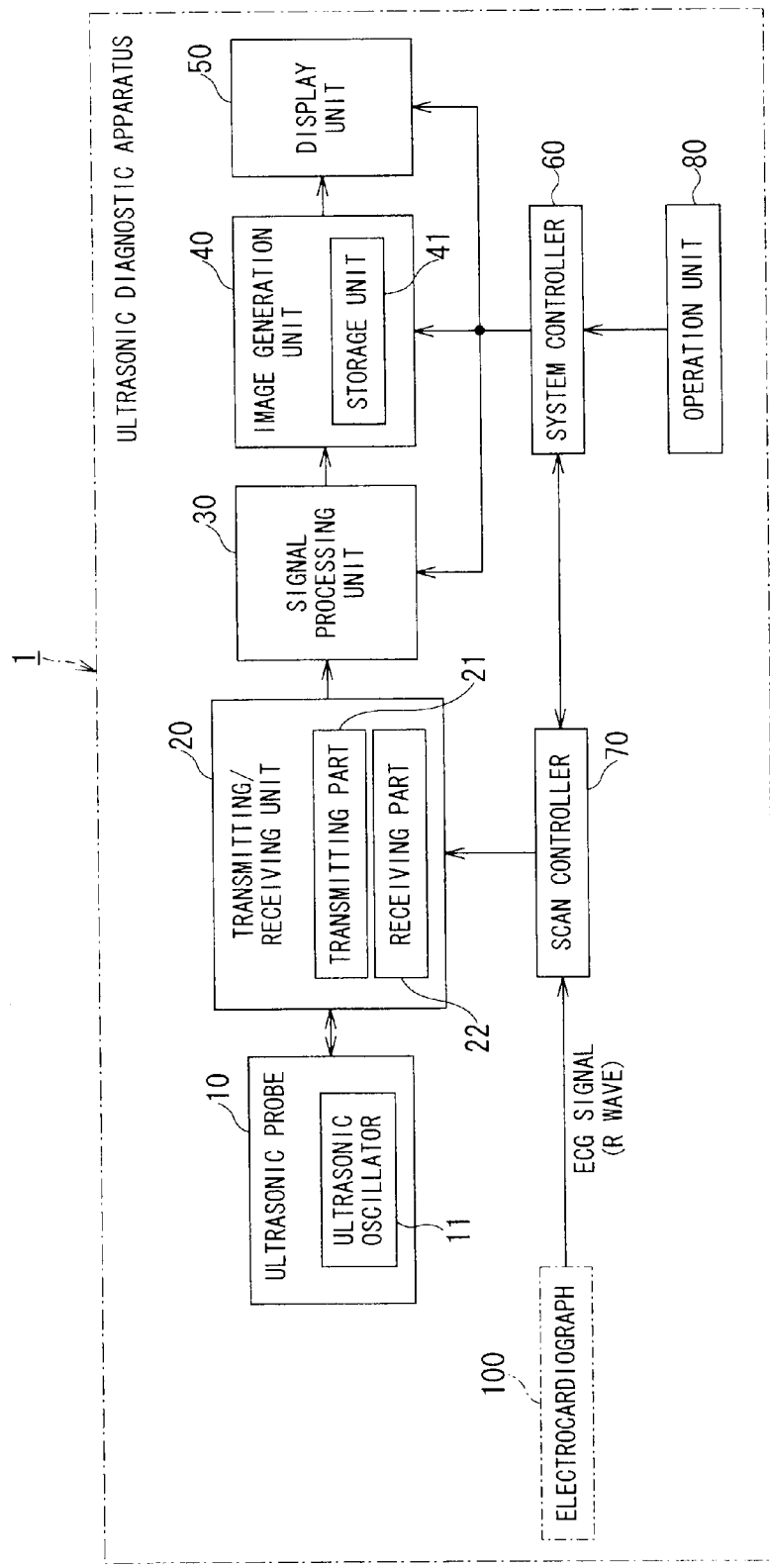
FIG. 2 is a block diagram illustrating an example of a configuration of an ultrasonic diagnostic apparatus according to an embodiment of the present invention.

FIG. 2 is a block diagram illustrating an example of a configuration of the ultrasonic diagnostic apparatus 1. The ultrasonic diagnostic apparatus 1 includes, for example, an ultrasonic probe 10, a transmitting/receiving unit 20, a signal processing unit 30, an image generation unit 40, a display unit 50, a system controller 60, a scan controller 70, an operation unit 80, and an electrocardiograph 100.

The ultrasonic probe 10 has a plurality of ultrasonic oscillators 11 arranged in the form of an array thereby to generate an ultrasonic pulse in accordance with a transmission pulse signal output from a transmitting part 21 of the transmitting/receiving unit 20 so that the generated ultrasonic pulse is transmitted toward a body under examination. If the ultrasonic probe 10 receives an ultrasonic reflection signal reflected from the body under examination, the ultrasonic probe 10 converts it into an electric signal and supplies the resultant electric signal to a receiving part 22 of the transmitting/receiving unit 20. In accordance with a beam scanning control signal output from the scan controller 70, the ultrasonic probe 10 scans the ultrasonic beam in the main scanning direction and the sub scanning direction.

The transmitting part 21 of the transmitting/receiving unit 20 generates the transmission pulse to be supplied to each ultrasonic oscillator 11 in accordance with a timing signal or the like generated by the scan controller 70. Furthermore, in accordance with the beam scanning control signal generated by the scan controller 70, the transmitting part 21 of the transmitting/receiving unit 20 sets a delay for each transmission pulse so as to define the scanning direction of the transmission ultrasonic beam.

If the reflection signal from the body under examination is supplied from each ultrasonic oscillator 11 to the receiving part 22 of the transmitting/receiving unit 20, the receiving part 22 of the transmitting/receiving unit 20 amplifies the received reflection signal and converts it from analog form into digital form. Furthermore, based on the beam scanning control signal generated by the scan controller 70, the receiving part 22 of the transmitting/receiving unit 20 sets a delay for the reflection signal of each ultrasonic oscillator 11 so as to determine the scanning direction of the received ultrasonic beam, and the receiving part 22 of the transmitting/receiving unit 20 adds the delay to each reflection signal. The resultant signal is supplied as a reflection signal of the beam to the signal processing unit 30.

The signal processing unit 30 performs signal processing such as a filtering process on the reflection signal supplied from the receiving part 22 and outputs the resultant signal to the image generation unit 40.

The image generation unit 40 includes a storage unit 41 disposed therein. The image generation unit 40 produces a sub volume image (data according to which to display an image (hereinafter referred to simply as image data)) by converting the reflection signal subjected to the signal processing, and sequentially and temporarily stores the produced sub volume image in the storage unit 41. The storage unit 41 has a storage capacity high enough to store image data obtained by scanning the full volume a plurality of times (for example, 4 times or more).

In the ultrasonic diagnostic apparatus 1 according to the present embodiment, three-dimensional image data of a full volume is produced by processing the sub volume images stored in the storage unit 41. In this processing, without being restricted by the order of data stored in the storage unit 41, i.e., the temporal order thereof, sub volume images are selected from a plurality of sub volume images corresponding to the same sub volume so that a full volume image with good spatial continuity can be produced from the selected sub volume images. A further detailed description thereof will be given later.

The image generation unit 40 performs processing such as a rendering process on the synthesized three-dimensional image data of the full volume thereby to generate a three-dimensional image viewed in a specified arbitrary direction or an image of a specified arbitrary section thereof. The generated image data is output to the display unit 50. The three-dimensional image data may be provided in the form of a moving image that is updated every frame time, for example, at 20 fps. The moving image data can be output in real time to the display unit 50 during diagnosis. The image data may be stored in a proper memory, and the moving image may be output in an off-line mode after diagnosis, or a still image extracted from the moving image may be output.

The display unit 50 is a display device such as a liquid crystal display configured to display the image output from the image generation unit 40.

The operation unit 80 is a man-machine interface that allows a user to set various diagnosis modes of the ultrasonic diagnostic apparatus 1 and various parameters associated with the respective diagnosis modes. In the present embodiment, the ultrasonic diagnostic apparatus 1 has a diagnosis mode in which motion of a beating heart can be displayed in the form of a three-dimensional moving image in synchronization with the ECG trigger signal (hereinafter, referred to as a triggered three-dimensional diagnosis mode). The ultrasonic diagnostic apparatus 1 is also operable in a conventional two-dimensional diagnosis mode. The setting as to the respective diagnosis modes and switching between them are performed via the operation unit 80.

The system controller 60 controls the whole ultrasonic diagnostic apparatus 1 in accordance with the diagnosis mode and various parameters set via the operation unit 80.

The scan controller 70 performs beam management on the ultrasonic beam and transmission/reception time management depending on the diagnosis mode. More specifically, in the triggered three-dimensional diagnosis mode, the scan controller 70 generates a trigger signal from an ECG signal (R wave) output from the electrocardiograph 100 and determines the beam scanning position (the main scanning direction and the sub scanning direction) for each sub volume in synchronization with the trigger signal and also determines various parameters associated with the repetitive scanning operation in the sub volume. The signals and the parameters are supplied to the transmitting/receiving unit 20 or the image generation unit 40. Furthermore, the scan controller 70 determines the various parameters associated with the transmission pulse such as the pulse repetition frequency of the ultrasonic beam and generates various timing signals based on the parameters of the transmission pulse.

Operation in Triggered Three-Dimensional Diagnosis Mode

The operation of the ultrasonic diagnostic apparatus 1 configured in the above-described manner is described below, in particular, on the operation in the triggered three-dimensional diagnosis mode.

Figure 3:
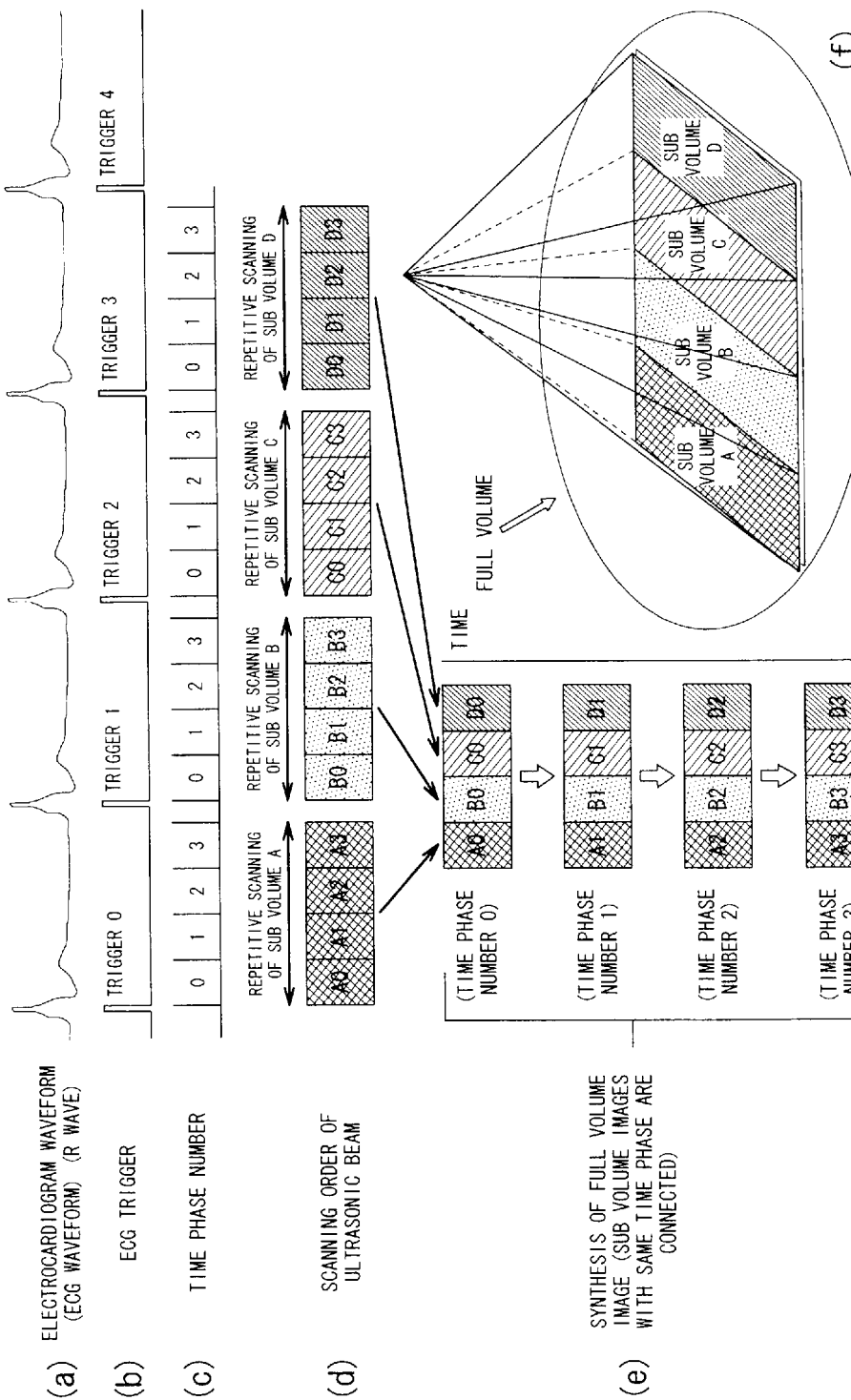
FIG. 3 is a diagram illustrating a concept of a general operation in a triggered three-dimensional diagnosis mode.

FIG. 3 illustrates the principle of the operation in the triggered three-dimensional diagnosis mode disclosed, for example, in U.S. Pat. No. 6,544,175. The triggered three-dimensional diagnosis mode is used mainly in diagnosis of a heart. In the triggered three-dimensional diagnosis mode, motion of a beating heart can be displayed as a three-dimensional moving image. In the triggered three-dimensional diagnosis mode, an ECG signal varying depending on the beat of a heart of a patient is input from the electrocardiograph 100, and a pulse signal called the ECG trigger signal is generated from the input ECG signal. As to the ECG signal, an R wave signal (see (a) in FIG. 3) having a form of a pulse that is output in an end period of diastole is generally used. The ECG signal is input to the scan controller 70. The scan controller 70 generates the ECG trigger signal by applying a properly determined threshold value to the input ECG signal (see (b) in FIG. 3). The ECG trigger signal is a signal synchronous with beating of a heart. When the heart beats 60 times every minute, the ECG trigger signal has a repetition period of 1 second.

In the triggered three-dimensional diagnosis mode, the whole diagnosis region (full volume) is divided into a plurality of sub volumes (blocks) and the sub volumes are sequentially scanned in response to one ECG trigger signal. For example, as shown in (f) of FIG. 3, the full volume is divided into four sub volumes A, B, C, and D, and the sub volumes are scanned sequentially in the order A, B, C, D in response to ECG trigger signals 0, 1, 2, and 3.

Each sub volume is scanned not once but a plurality of times (N times). In the example shown in FIG. 3, the scanning is performed 4 times (N=4). The scanning time T needed to scan each sub volume once corresponds to the frame time (the reciprocal of the frame rate) of a moving image as described in further detail later, and thus, to obtain a smooth moving image, it is desirable that the scanning time T be about 50 ms (=1/20 fps) or smaller. If it is assumed that the repetition period of the ECG trigger signal is 1 second and the unit scanning time is 50 ms, then the number of repetitions of scanning for each sub volume becomes 20 (N=20). In the example shown in FIG. 3, for the purpose of simplicity of explanation, the number of repetitions of scanning for each sub volume is assumed to be 4 (N=4).

When the same sub volume is being scanned repeatedly, the heart periodically beats, and thus image data generated during the repetitive scanning process is different depending on the time phase, i.e., the delay with respect to the ECG trigger.

In (c) of FIG. 3, time phases are defined for the respective scan repetition periods and time phase numbers are assigned to the respective time phases in the order "0", "1", "2", "3" starting from the time phase closest to the ECG trigger signal. In (d) of FIG. 3, each of the scanning periods of the sub volumes are identified by a combination of a time phase number (one of "0", "1", "2", and "3") and a sub volume name (one of "A", "B", "C", and "D") such as "A0" to "A3", "B0" to "B3", "C0" to "C3", and "D0" to "D3", and the scanning periods are arranged in the order in which they are scanned with the ultrasonic beam.

The signal processing unit 30 performs signal processing on the reflection signal received from the body under examination and outputs, in real time, the resultant reflection signal to the image generation unit 40 in the order corresponding to the scanning order.

In (e) of FIG. 3, a manner of synthesizing a full volume in a process performed by the image generation unit 40 is shown. Note that the manner of synthesizing a full volume shown in (e) of FIG. 3 is that generally employed in the conventional triggered three-dimensional diagnosis mode. As described later, an improved synthesis method is employed in the ultrasonic diagnostic apparatus 1 according to the present embodiment. Before the improved method according to the present embodiment, the concept of the conventional method is described below.

The image generation unit 40 extracts data with an equal time phase number from the data of the sub volumes identified by the time phase numbers, and connects the data corresponding to the sub volumes A, B, C, and D so as to obtain synthesized data of the full volume. Note that even for sub volume data having an equal time phase number, there is a time difference corresponding to one period of the ECG trigger signal between adjacent sub volumes. However, the change in shape of the heart can be regarded as having the same periodicity as that of the ECG trigger signal, and thus the full volume image obtained by connecting the sub volumes with the same time phase number has good spatial continuity.

At a time when data of the sub volume "D0" corresponding to the time phase number "0" is acquired, data of the sub volumes "A0", "B0", and "C0" has already been acquired. Thus, at this point of time, the full volume image corresponding to the time phase number "0" is generated.

At a time when next data of the sub volume "D1" corresponding to the time phase number "1" is acquired, data of the sub volumes "A1", "B1", and "C1" has already been acquired. Thus, at this point of time, the full volume image corresponding to the time phase number "1" is generated. Subsequently, full volume images for time phase numbers 2 and 3 are generated in a similar manner.

If the scanning "D3" for the sub volume D is completed, the scanning is repeated from the sub volume A. In this case, the data "A0" obtained in this scanning operation replaces the full volume data "A0" with the time phase number "0" generated in the previous scanning, and thus the full volume image with the time phase number "0" is updated.

As described above, the full volume image is generated and updated every one scanning period T of each sub volume.

The technique described above allows the obtained image to be seemed as if the whole full volume were scanned every one scanning period of one sub volume although the actual scanning time for the whole full volume is longer. That is, it is possible to obtain a full volume image updated at a frame rate that is apparently, but not actually, equal to the frame rate of sub volumes.

For example, when the highest possible frame rate of the full volume is limited to 5 fps due to a limitation on the scanning time, if the full volume is divided into four sub volumes, it is allowed to scan each sub volume in a scanning period that is one-fourth the scanning time for the full volume, and thus the frame rate of sub volume image becomes 20 fps that is 4 times greater than that of the full volume image. In the triggered three-dimensional diagnosis mode, the frame rate of the full volume image is equal to the frame rate of the sub volume image, and thus it is possible to achieve the frame rate as high as 4 times the frame rate achieved in the conventional technique.

As described above, in the triggered three-dimensional diagnosis mode, it is possible to obtain a high-resolution image with a high frame rate for a great three-dimensional diagnostic region, and thus it is possible to generate a real-time moving image for a moving diagnostic object such as a heart.

The heartbeat period of human beings is not necessarily constant. On the contrary, even persons with a normal and healthy body have a variation of about 10% in the heartbeat period. In particular, in the case of patients having a heart disease, a greater variation in heartbeat period can occur.

As described above, a great fluctuation of the heartbeat period can cause a possibility that when a full volume image is synthesized by connecting sub volume images having the same time phase number, no sub volume image is obtained for great time phase numbers (sub volume images with time phase numbers close to a next ECG trigger signal).

In order to ensure the spatial continuity for the full volume image obtained by connecting sub volume images having the same time phase number acquired at different times, it is required that the heartbeat period should be substantially constant over a period in which the sub volume images are acquired. Therefore, when a complete set of sub volume images having the same time phase number is obtained, if there is a great difference in heartbeat period among the acquired sub volume images, there is a possibility that spatial continuity is not achieved for a synthesized full volume image. This is because a great difference in heartbeat period can cause a difference in the state of a heart in terms of contraction or relaxation even for the same time phase number.

First Method of Synthesizing Full Volume Image

In the ultrasonic diagnostic apparatus 1 according to the present embodiment, to solve the above-described problem, sub volume images obtained during a period in which a full volume is scanned a plurality of times are stored in the storage unit 41.

Figure 4:
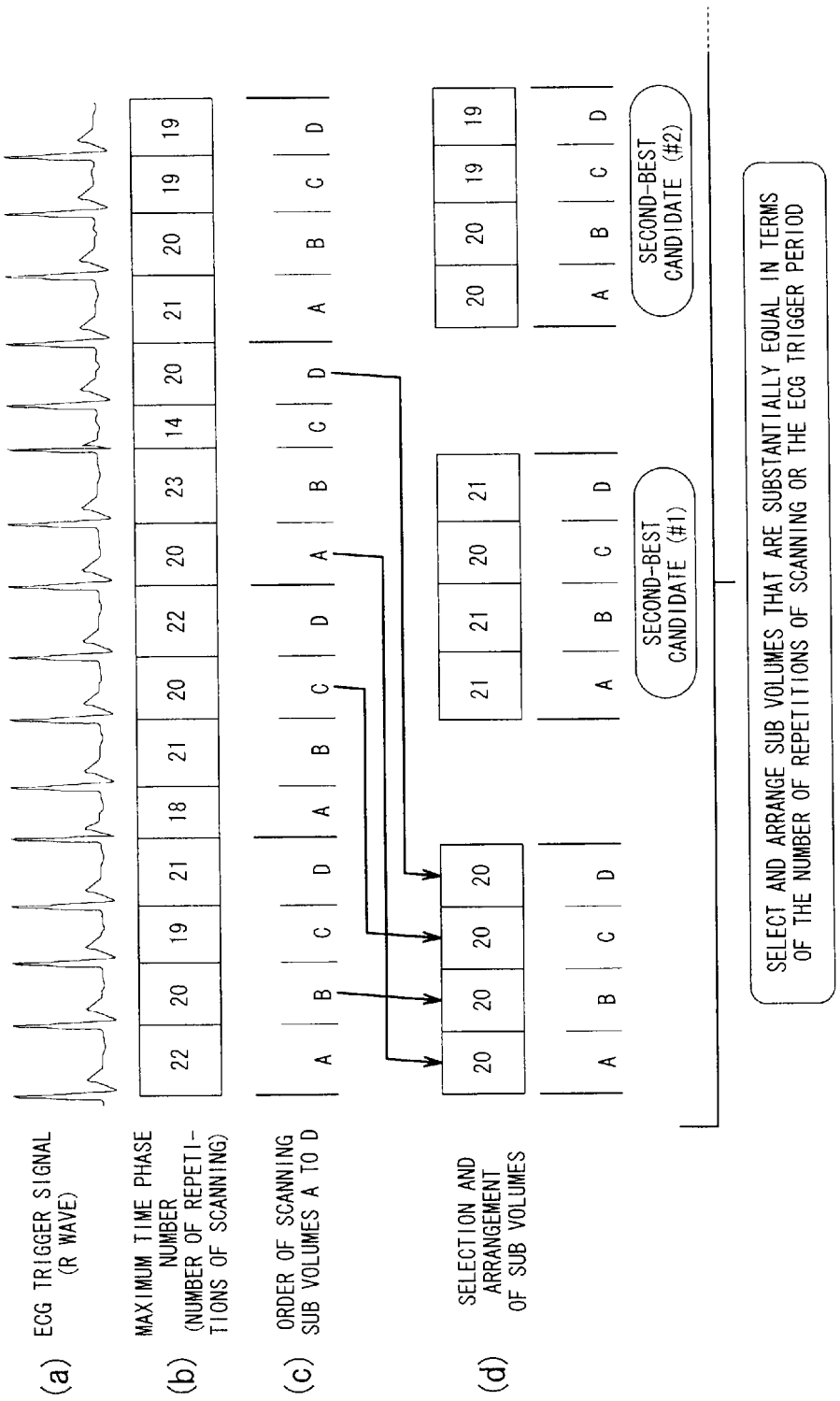
FIG. 4 is a diagram illustrating a method (first method) of synthesizing a full volume image.

FIG. 4 is a diagram illustrating a method (first method) of synthesizing a full volume image. In FIG. 4, (a) illustrates an example of an ECG trigger signal that varies in repetition period in response to a variation of a heartbeat period. Because the scanning of any sub volume is started in response to the ECG trigger signal, the variation in the length of the repetition period of the ECG trigger signal causes the number of repetitions of scanning within each repetition period (i.e., the maximum time phase number) to vary depending on the heartbeat period. In FIG. 4, (b) illustrates a manner in which the maximum time phase number varies in the range from 14 to 23 depending on the heartbeat period shown in (a) of FIG. 4.

In FIG. 4, (c) illustrates the order in which sub volume images obtained by scanning the sub volumes A to D are input to the image generation unit 40. In this example shown in (c) of FIG. 4, data obtained during a period in which the full volume is scanned successively 4 times is input. The data obtained during this period is stored in the storage unit 41. During one-time scanning of the full volume, 4 sub volumes A, B, C, and D are scanned. Therefore, 16 sub volume images are temporarily stored in the storage unit 41. In this case, 4 sub volume images are stored for each sub volume.

When the heartbeat period is assumed to be 1 second, sub volume image data obtained in 16 seconds is stored in the storage unit 41. If the storage unit 41 is completely filled with data, data is sequentially deleted in the order of acquisition time from oldest one so that the data is updated by newly input sub volume image data.

In the conventional technique, a full volume image is synthesized using only most recent four sub volume images of sub volumes A, B, C, and D stored in the image generation unit 40. For example, only four sub volume images A, B, C, and D at the leftmost positions in (c) of FIG. 4 are used. In this case, the four sub volumes images have different maximum time phase numbers 22, 20, 19, and 21, respectively. Thus, in a region close to the maximum time phase numbers, it is impossible to correctly connect four sub volume images A, B, C, and D. When sub volume images with the same time phase number, for example, 10, are connected, the differences in heartbeat period lead to differences in the state of the heart in terms of contraction or relaxation, and thus the synthesized full volume image does not have good spatial continuity.

In view of the above, in the method (first method) of synthesizing the full volume image according to the present embodiment, 4 sub volume images A, B, C, and D having substantially the same heartbeat period or maximum time phase number are selected not from the most recent 4 sub volume images but from 16 sub volume images stored in the storage unit 41 without being restricted on the temporal order, and the selected sub volume images are connected. Herein, the expression "substantially the same" means that the heartbeat period or the maximum time phase number is exactly the same or is within a predetermined range around a predetermined reference value.

In an example shown on the leftmost side of (d) of FIG. 4, 4 sub volume images A, B, C, and D all having a maximum time phase number of 20 are selected, and a full volume image is synthesized by sequentially connecting these images in the order A, B, C, D.

In examples shown in the middle and on the rightmost side of (d) of FIG. 4, 4 sub volume images A, B, C, and D having a time phase number falling within a range of ±1 around a reference value of 20 are selected and full volume images are synthesized. The resultant full volume images are given as a second-best combination candidate #1 and a second-best combination candidate #2, respectively. In the case where a combination of sub volumes A, B, C, and D having the same maximum time phase number is not available, a most proper combination is selected from these second-best candidates.

In the method (first method) of synthesizing a full volume image according to the present embodiment, sub volume images A, B, C, and D having substantially the same maximum time phase number are selected, thereby reducing the probability that it is impossible to correctly connect sub volume images A, B, C, and D for time phase numbers close to the maximum time phase number. Because maximum time phase numbers are equal or substantially equal for sub volumes used in synthesis (because the heartbeat period is substantially equal), it is possible to achieve better spatial continuity of the synthesized full volume image.

Figure 5:
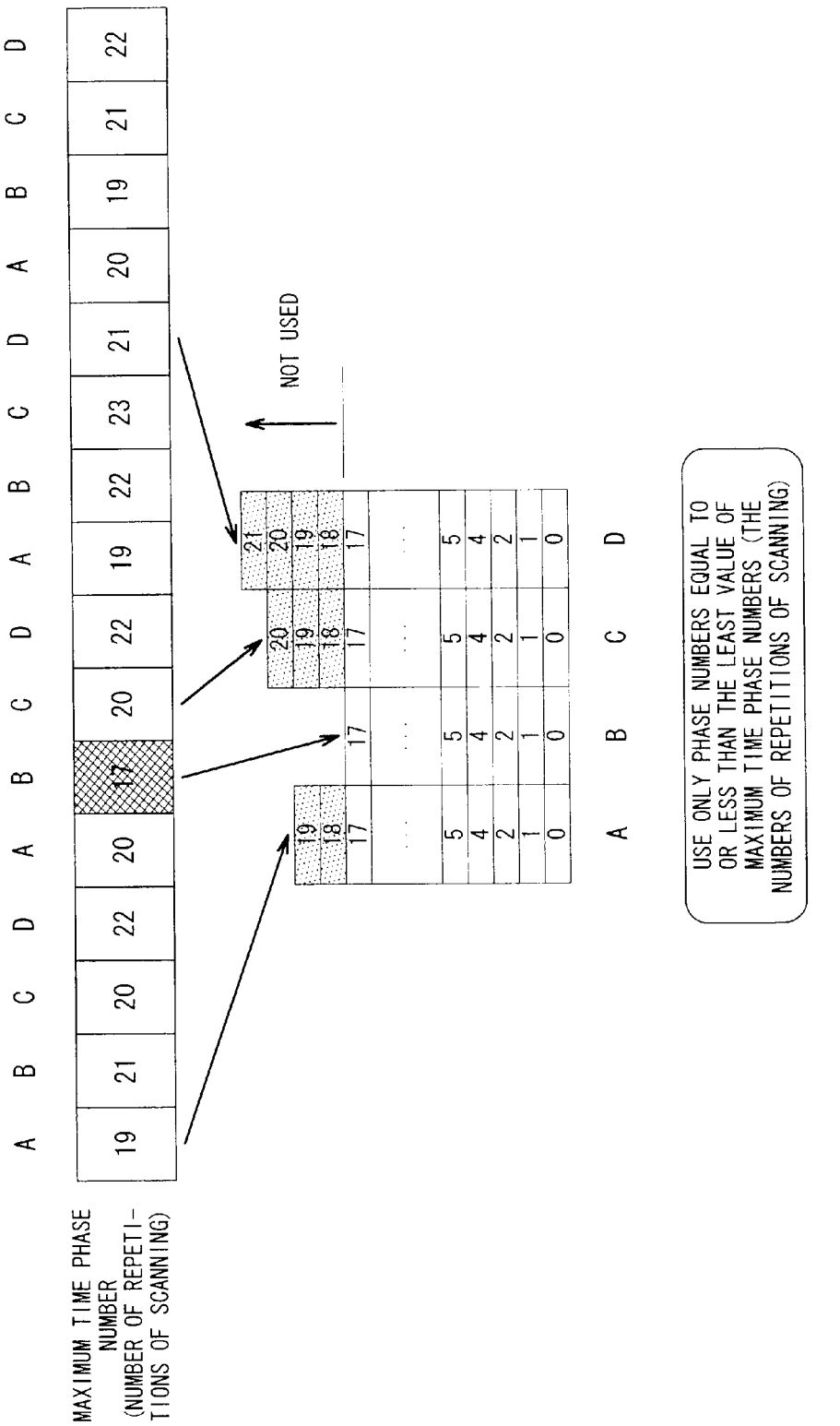
FIG. 5 is a diagram illustrating a first example of a modification to the method (first method) of synthesizing a full volume image.

FIG. 5 illustrates a first example of a modification to the method (first method) of synthesizing a full volume image. In this first modification, a least value (17, in the example shown in FIG. 5) is selected from maximum time phase numbers associated with 16 sub volume images stored in the storage unit 41, and a full volume image is synthesized by combining sub volume images having maximum time phase numbers close to the selected least value without using sub volume images having time phase numbers greater than the selected least value.

This first modification makes it possible to prevent the problem that 4 sub volume images A, B, C, and D cannot be connected for time phase numbers close to the maximum time phase number.

Figure 6:
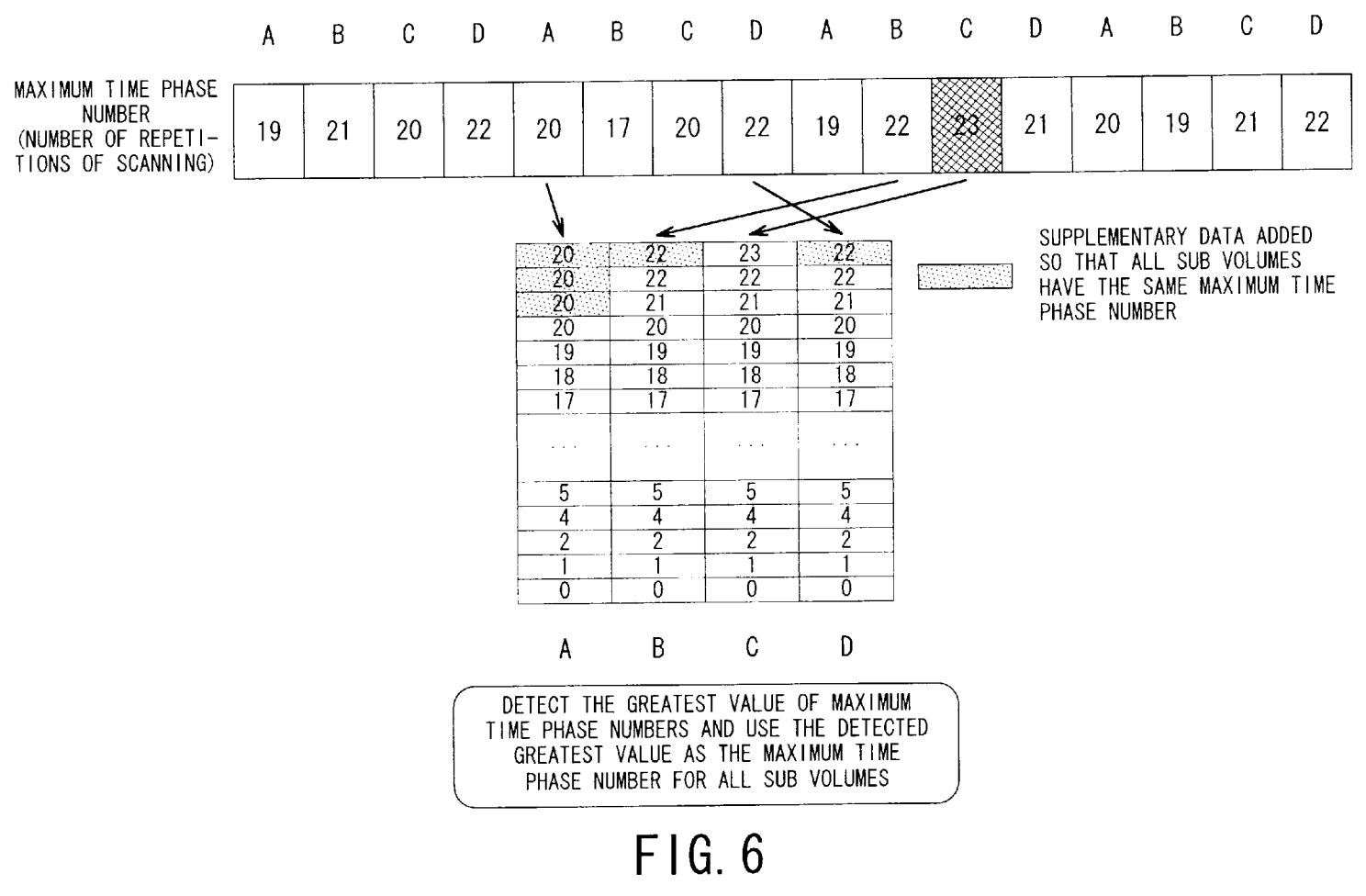

FIG. 6 is a diagram illustrating a second example of a modification to the method (first method) of synthesizing a full volume image. In this second modification, as opposed to the first modification, a greatest value (23, in the example shown in FIG. 6) is selected from maximum time phase numbers associated with 16 sub volume images stored in the storage unit 41, and a full volume image is synthesized by combining sub volume images having maximum time phase numbers close to the selected greatest value. When a maximum time phase number close to the selected greatest value is not found for a particular sub volume image, a sub volume image having a time phase number that is the greatest within this sub volume is copied and used as a complement.

In the second modification described above, it is possible to synthesize a full volume image using data including a greater number of time phases than in the first modification although some data may be quasi-data. Thus, it becomes possible to prevent the problem that 4 sub volume images A, B, C, and D cannot be connected for time phase numbers close to the maximum time phase number.

Figure 7:
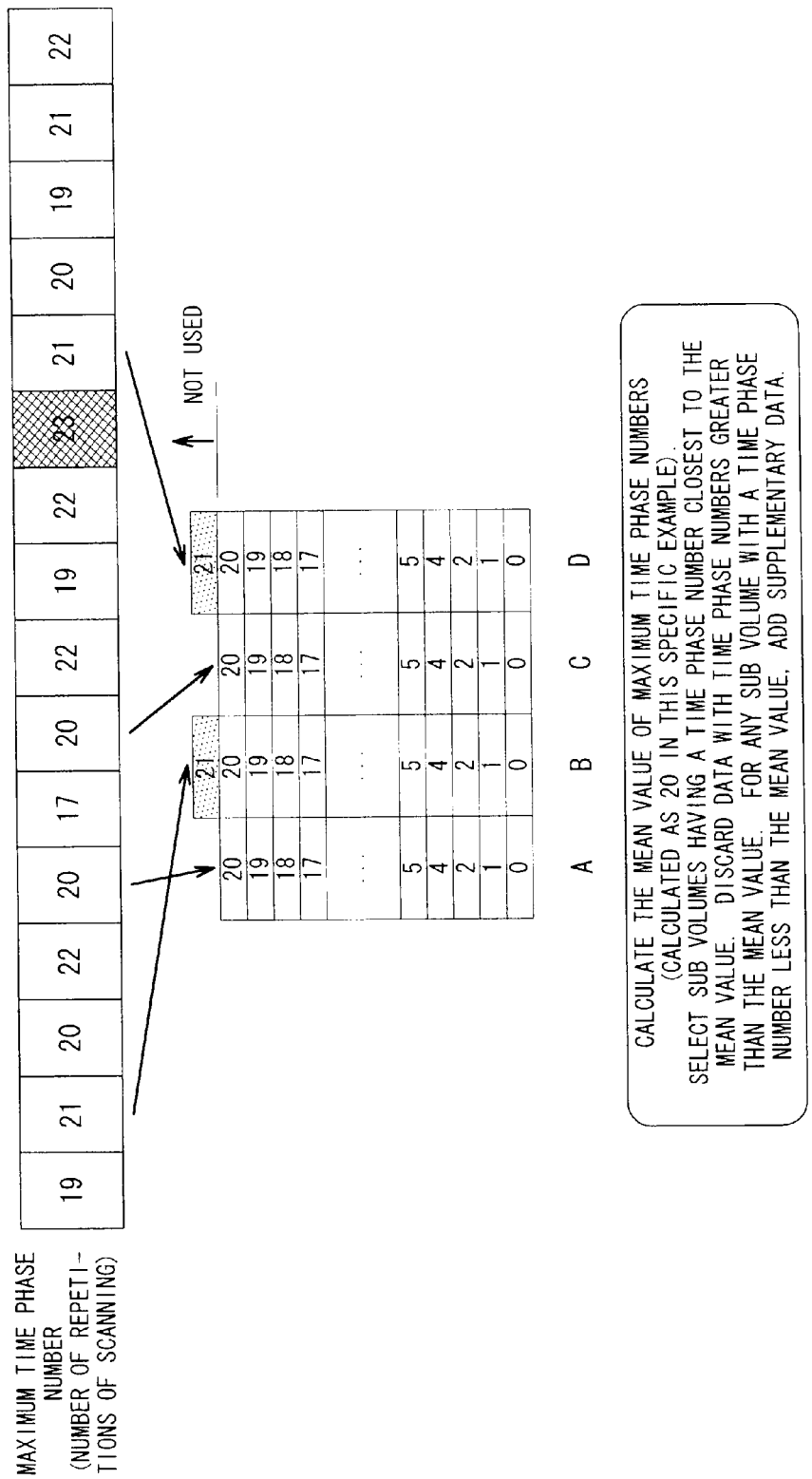
FIG. 7 is a diagram illustrating a third example of a modification to the method (first method) of synthesizing a full volume image.

FIG. 7 is a diagram illustrating a third example of a modification to the method (first method) of synthesizing a full volume image. In this third modification, the mean value is determined for the maximum time phase numbers of the 16 sub volume images stored in the storage unit 41 (the mean value is 20, in the example shown in FIG. 7), and a full volume image is synthesized by combining sub volume images having maximum time phase numbers equal to or close to the mean value. For any sub volume whose maximum time phase number is smaller than the mean value, a sub volume image having a greatest time phase number within the sub volume is copied and used as a complement. On the other hand, for any sub volume whose maximum time phase number is greater than the mean value, sub volume images having a time phase number greater than the mean value are not used in the synthesis of the full volume image.

Even if a fluctuation in the heartbeat period occurs, the occurrence frequency is generally high for heartbeat period values close to the mean value, while the occurrence frequency is low for heartbeat period values greatly different from the mean value. Thus, in the third modification, there is a greater probability that sub volume images having an equal or nearly equal heartbeat period can be selected from sub volume images stored in the storage unit 41.

In the first embodiments (including various modifications), the timing of selecting sub volumes may be determined according to one of two approaches described below.

A first approach is to first acquire a plurality of pieces of sub volume data and store them (that is, temporarily freeze the acquired data), and then select sub volumes. In this approach, a criterion for selection is set in advance. During a real-time operation, a full volume is acquired and displayed in accordance with the conventional technique. However, when freezing is performed, automatic selection of sub volumes according to the criterion and rearrangement are immediately performed, and the result is displayed. A proper user interface may be provided so that a user is allowed to perform selection and rearrangement of sub volumes at a desired time.

A second approach is to sequentially perform selection and rearrangement of sub volumes during a real-time operation. In this second approach, a full volume is acquired and displayed in accordance with the conventional technique until a first full volume is completely acquired. Once the full volume is acquired, each time data of one sub volume is further obtained thereafter, an optimum combination of sub volumes is re-selected and the result is displayed. In this approach, in order to ensure the real-time operation, the selection of sub volumes may be performed for those prior to a sub volume being currently subjected to the acquisition operation, and the combination of sub volumes may be re-selected when acquisition is started for the next sub volume thereby achieving high reliability in the operation.

Second Method of Synthesizing Full Volume Image

Figure 8:
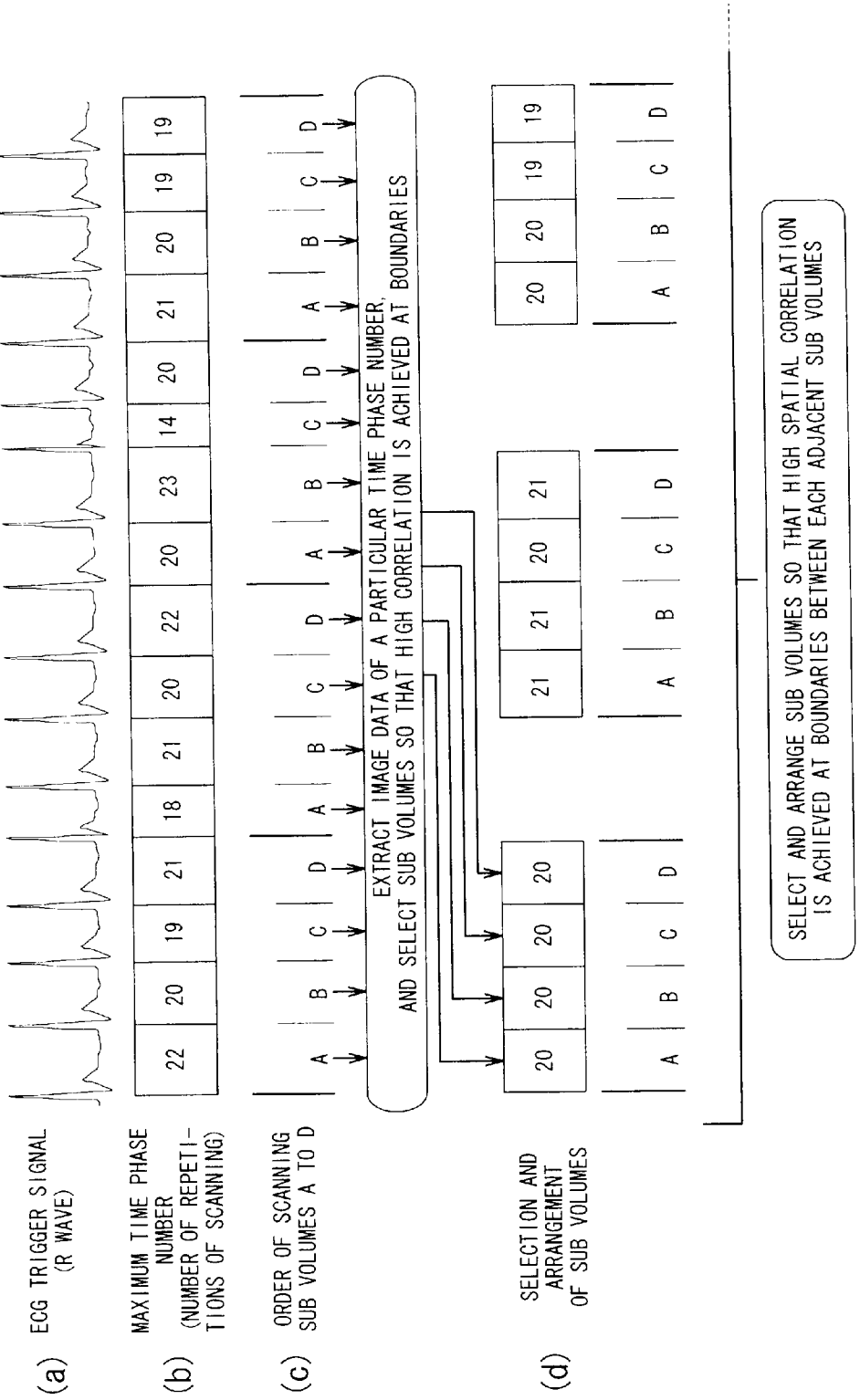
FIG. 8 is a diagram illustrating a method (second method) of synthesizing a full volume image.
Figure 9:
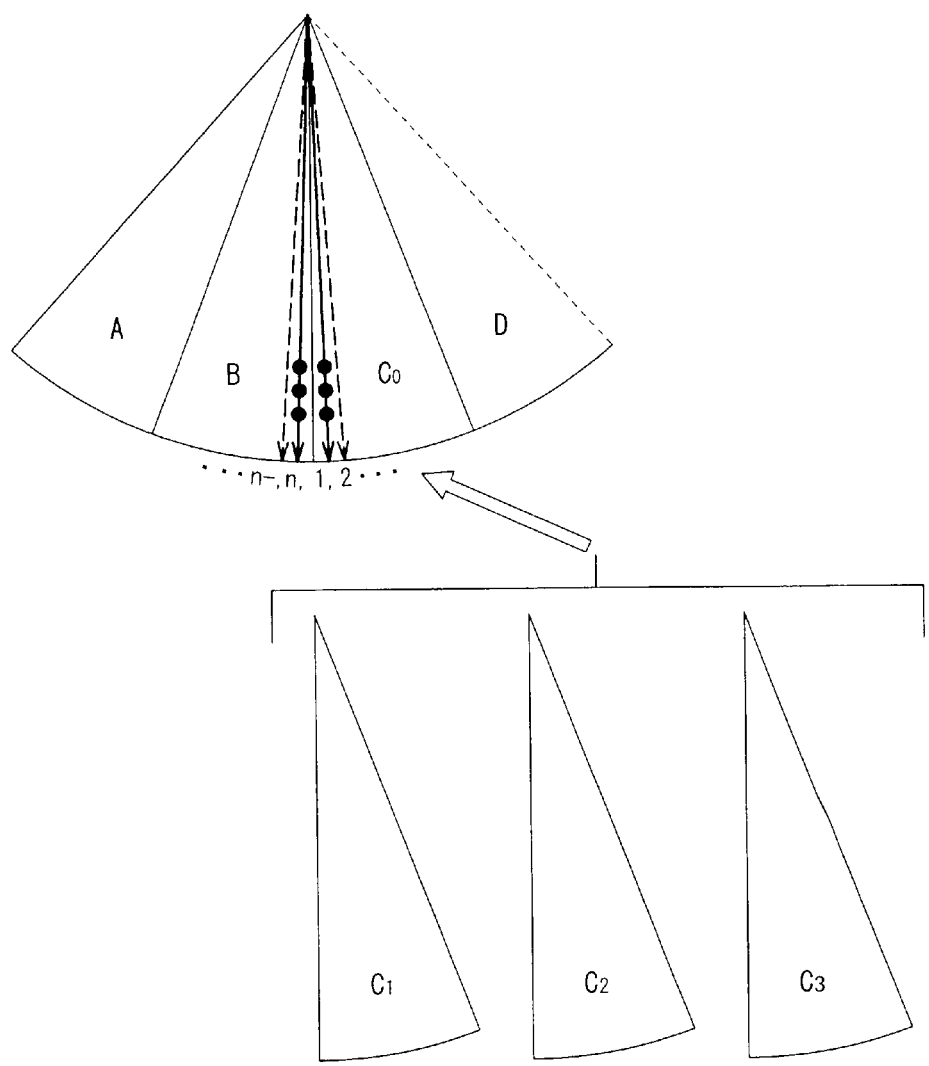
FIG. 9 is a diagram also a method (second method) of synthesizing a full volume image.

FIGS. 8 and 9 illustrate a second method of synthesizing a full volume image. In the first method described above, good spatial continuity is achieved by selecting sub volume images having a substantially equal heartbeat period (or maximum time phase number) and synthesizing a full volume image from the selected sub volume images. In the second method, in contrast to the first method, the index indicating the spatial correlation between adjacent sub volume images is directly calculated, sub volume images with highest spatial correlation are selected, and a full volume image is synthesized from the selected sub volume images.

In the second method, full volume scan data for a plurality of periods (4 periods, for example) is stored in the storage unit 41 in a similar manner to the first method.

Sub volume image data associated with a particular time phase number (for example, time phase number 10) is then extracted. In an example shown in (c) of FIG. 8, 16 sub volume images with a particular time phase number are stored in the storage unit 41. Sub volume images having high spatial correlation between adjacent sub volumes are selected from the sub volume images stored in the storage unit 41, and the selected sub volume images are connected.

FIG. 9 illustrates a selection method. In FIG. 9, it is assumed that a combination of a sub volume A and a sub volume B has already been determined. Under this assumption, FIG. 9 illustrates an example of a process of selecting a sub volume C adjacent to the sub volume B is shown. In this example, 4 sub volume images ($C_0$, $C_1$, $C_2$, and $C_3$) of the sub volume C are stored in the storage unit 41. The index indicating the spatial correlation between the sub volume B and the sub volume C is calculated for each of these sub volume images $C_0$, $C_1$, $C_2$, and $C_3$, and a sub volume image C having highest spatial correlation is selected. The selected sub volume image C is then connected to the sub volume image B.

A specific example of the index indicating the spatial correlation is the sum of differences (absolute values of differences) between pixel values of pixels located on a boundary line (line n) of the sub volume image B and pixel values of corresponding pixels located on a boundary line (line 1) of the sub volume line C. The closer to zero the sum is, the higher the spatial correlation is.

In the second method, as described above, the index indicating the spatial correlation between adjacent sub volume images is directly calculated, and a full volume image is synthesized by connecting sub volume images with highest spatial correlation, and thus high spatial continuity can be achieved.

Method of Assisting in Synthesizing Full Volume Image

In the first and second methods described above, because the combination of sub volume images is automatically determined by a machine (the image generation unit 40 of the ultrasonic diagnostic apparatus 1), the resultant combination is not always evaluated as optimal by a user when the user evaluates the full volume image as a moving image.

In view of the above, in the ultrasonic diagnostic apparatus 1 according to the present embodiment, there is provided a selection/display unit configured to allow a user to change the combination of sub volume images or select a most suitable full volume image from a plurality of full volume images synthesized from different combinations of sub volume images.

Figure 10:
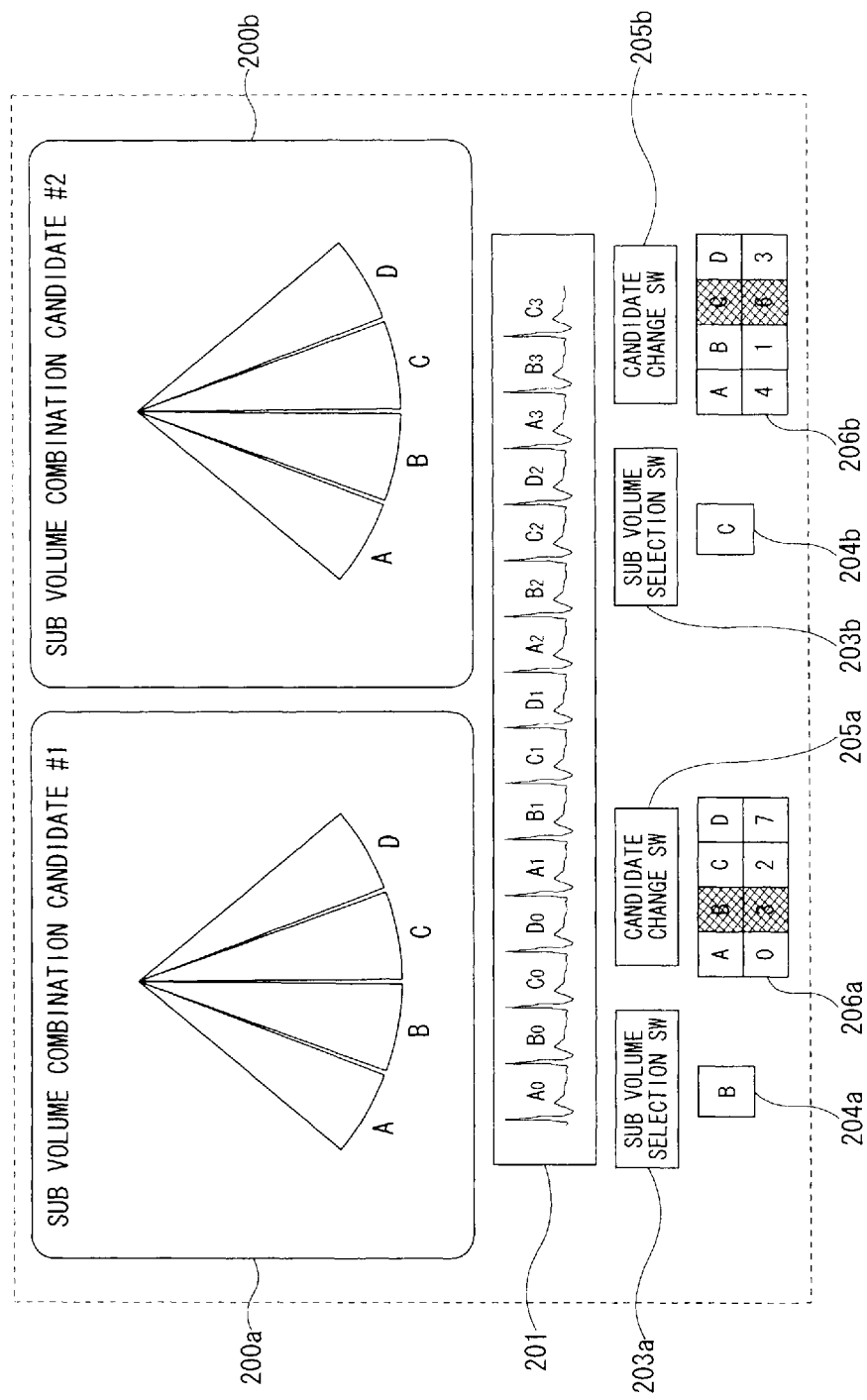
FIG. 10 is a diagram illustrating an example of a unit configured to select/display full volume image combination candidates.

FIG. 10 illustrates an example of the selection/display unit. The ultrasonic diagnostic apparatus 1 includes candidate image display units 200a and 200b configured to display full volume image candidates in a side-by-side manner, and a selectable sub volume display unit 201 configured to display selectable sub volumes. Note that each selectable sub volume is identified by identification information such as "A0", "B0", etc. The ultrasonic diagnostic apparatus 1 further includes sub volume selection units 203a and 203b configured to specify sub volumes to be selected, selected sub volume display units 204a and 204b configured to display selected sub volumes, candidate change units 205a and 205b configured to change sub volume candidates to be combined, and combination display units 206a and 206b configured to display current combinations. Note that the various display units described above are units displayed on a display screen, for example, of the display unit 50. The the selection units and the change units are units provided, for example, on the operation unit 80.

On the candidate image display units 200a and 200b, full volume images synthesized from combinations of sub volume images selected by the ultrasonic diagnostic apparatus 1 are displayed in the form of moving images. For example, a full volume image synthesized from a combination of sub volume images shown on the leftmost side of (d) in FIG. 4 is displayed as a combination candidate #1 is displayed on the candidate image display unit 200a, and a full volume image synthesized from a combination of sub volume images shown on in the middle of (d) in FIG. 4 is displayed as a combination candidate #2 is displayed on the candidate image display unit 200b.

Although in this example, two full volume image candidates are displayed in the side-by-side manner, three or more full volume image candidates may be displayed in parallel. Only single full volume image may be displayed at a time, and the image being displayed may be switched at proper time intervals so as to sequentially display a plurality of full volume image candidates.

Thus, a user is allowed to perform a visual evaluation on the displayed full volume image candidates, and is allowed to select a proper full volume image from the candidates.

The user is also allowed to change the combination selected by the ultrasonic diagnostic apparatus 1. The change may be performed by operating the sub volume selection units 203a and 203b and the candidate change units 205a and 205b. The change in terms of the combination is immediately reflected on the full volume image candidates displayed on the candidate image display units 200a and 200b, and thus the user can evaluate in real time the result.

As described above, the ultrasonic diagnostic apparatus 1 and the method of controlling it according to the present embodiment are capable of preventing the synthesized image from having spatial/temporal discontinuity regardless of whether the heartbeat period varies.

Note that the present invention is not limited to details of the embodiments described above, but many modifications are possible without departing from the spirit and scope of the present invention. Elements disclosed in the embodiments described above may be properly combined to embody the invention in various aspects. One or more elements may be removed from the configurations disclosed in the embodiments described above. Elements disclosed in different embodiments may be combined.

What is claimed is:

1. An ultrasonic diagnostic apparatus, comprising:
a scan controller configured to scan sub volumes, each sub volume being obtained by dividing a full 3D volume to be imaged, while changing the sub volume every ECG trigger signal so as to acquire a plurality of data sets respectively corresponding to a plurality of heart beats, each data set of the plurality of data sets corresponding to one of the plurality of heart beats and including a plurality of sub data sets, each sub data set within the data set being acquired at a different time phase; and
image generation circuitry configured
to select specific sub data sets, including one for each sub volume, for generating an image of the full 3D volume among the acquired plurality of data sets by maximizing a spatial correlation between adjacent sub data sets in the specific sub data sets, and
to connect the specific sub data sets to generate images of the full 3D volume at the different time phases.

2. The ultrasonic diagnostic apparatus according to claim 1, wherein the image generation circuitry is further configured to select the specific sub data sets such that the spatial correlation between the adjacent sub data sets is maximized.

3. A method, comprising:
scanning sub volumes, each sub volume being obtained by dividing a full 3D volume to be imaged, while changing the sub volume every ECG trigger signal so as to acquire a plurality of data sets respectively corresponding to a plurality heart beats, each data set of the plurality of data sets corresponding to one of the plurality of heart beats and including a plurality of sub data sets, each sub data set within the data set being acquired at a different time phase;
selecting specific sub data sets, including one for each sub volume, for generating an image of the full 3D volume among the acquired plurality of data sets by maximizing a spatial correlation between adjacent sub data sets in the specific sub data sets; and
connecting the specific sub data sets to generate images of the full 3D volume at the different time phases.

4. The method of claim 3, wherein
in the selecting step, the specific sub data sets are selected such that the spatial correlation between the adjacent sub data sets is maximized.

5. The ultrasonic diagnostic apparatus according to claim 1, wherein
the image generation circuitry is configured to select the specific sub data sets in accordance with a spatial arrangement order of the data sets, without being restricted by a temporal acquisition order of the data sets.

6. The method claim 3, wherein
in the selecting step, the specific sub data sets are selected in accordance with a spatial arrangement order of the data sets, without being restricted by a temporal acquisition order of the data sets.

\* \* \* \* \*